(12) United States Patent
Ferrara

(10) Patent No.: US 9,345,639 B2
(45) Date of Patent: May 24, 2016

(54) SYSTEM FOR FACILITATING PREPARATION OF MEDICATION DOSES

(71) Applicant: Kenneth D. Ferrara, Rusk, TX (US)

(72) Inventor: Kenneth D. Ferrara, Rusk, TX (US)

( * ) Notice: Subject to any disclaimer, the term of this patent is extended or adjusted under 35 U.S.C. 154(b) by 0 days.

(21) Appl. No.: 14/941,219

(22) Filed: Nov. 13, 2015

(65) Prior Publication Data

US 2016/0067143 A1 Mar. 10, 2016

Related U.S. Application Data

(63) Continuation-in-part of application No. 14/850,325, filed on Sep. 10, 2015, which is a continuation of application No. 12/196,667, filed on Aug. 22, 2008, now Pat. No. 9,159,249, which is a continuation of application No. 11/563,901, filed on Nov. 28, 2006, now abandoned.

(60) Provisional application No. 60/783,111, filed on Mar. 16, 2006.

(51) Int. Cl.
*A61M 5/00* (2006.01)
*A61J 1/18* (2006.01)

(52) U.S. Cl.
CPC ............... *A61J 1/18* (2013.01); *A61J 2200/76* (2013.01); *A61J 2205/20* (2013.01)

(58) Field of Classification Search
CPC ............. A61M 2005/3125; A61M 2205/6081; A61M 2005/3126; A61M 5/3129; A61M 5/31511; A61M 5/31525
USPC ......................................................... 40/324
See application file for complete search history.

(56) References Cited

U.S. PATENT DOCUMENTS

| | | | |
|---|---|---|---|
| 2,031,892 A | 2/1936 | Johnson | |
| 2,410,351 A | 10/1946 | Lockhart | |
| 2,616,051 A * | 10/1952 | Daniels ..................... | G01T 1/11 206/305 |
| 3,391,694 A | 7/1968 | Spaeth | |
| 3,574,957 A | 4/1971 | Bello-Bridick | |
| 3,885,562 A | 5/1975 | Lampkin | |
| 4,921,277 A | 5/1990 | McDonough | |
| 5,046,609 A | 9/1991 | Mangini et al. | |
| 5,376,081 A | 12/1994 | Sapienza | |
| 5,377,879 A | 1/1995 | Isaacs | |
| 5,468,224 A * | 11/1995 | Souryal ................... | A61K 9/08 604/500 |
| 5,692,640 A | 12/1997 | Caulfield et al. | |
| 5,979,698 A | 11/1999 | Deal | |
| 5,984,901 A | 11/1999 | Sudo et al. | |
| 6,120,481 A | 9/2000 | Rennert et al. | |
| 6,132,416 A | 10/2000 | Broselow | |

(Continued)

*Primary Examiner* — Shin Kim
(74) *Attorney, Agent, or Firm* — Klemchuk LLP; Kirby B. Drake

(57) ABSTRACT

Delivery cups may be provided to facilitate preparation of medication doses and may include color bands extending about at least a portion of an exterior of each delivery cup. Each color band may correspond to a predetermined volumetric measurement or dosage of medication. Each delivery cup may provide a height that may be proportional to at least one of a maximum volume and a maximum volumetric measurement. Further, each delivery cup may provide one or more additional color bands that may represent volumetric measurements that may be less than that associated with the first color band. Each delivery cup may further provide a portion of the delivery cup that may be provided to fit inside of a medicine bottle and may be provided to a seal an opening of the medicine bottle. Each delivery cup may also provide a handle for dispensing fluid from the delivery cup.

16 Claims, 9 Drawing Sheets

(56) References Cited

U.S. PATENT DOCUMENTS

| | | |
|---|---|---|
| 6,802,279 B1 | 10/2004 | Johnson |
| 9,159,249 B2 | 10/2015 | Ferrara |
| 2004/0024365 A1 | 2/2004 | Bonnier |
| 2004/0024368 A1 | 2/2004 | Broselow |
| 2004/0071666 A1* | 4/2004 | Ferrara .............. A61K 38/1793 424/93.7 |
| 2007/0214692 A1* | 9/2007 | Ferrara ................. A61J 1/2096 40/324 |
| 2008/0067191 A1* | 3/2008 | Ferrara ................. G01F 11/027 222/41 |
| 2008/0306438 A1* | 12/2008 | Ferrara ................. A61J 1/2096 604/78 |
| 2015/0374584 A1* | 12/2015 | Ferrara ................. A61J 1/2096 604/404 |

\* cited by examiner

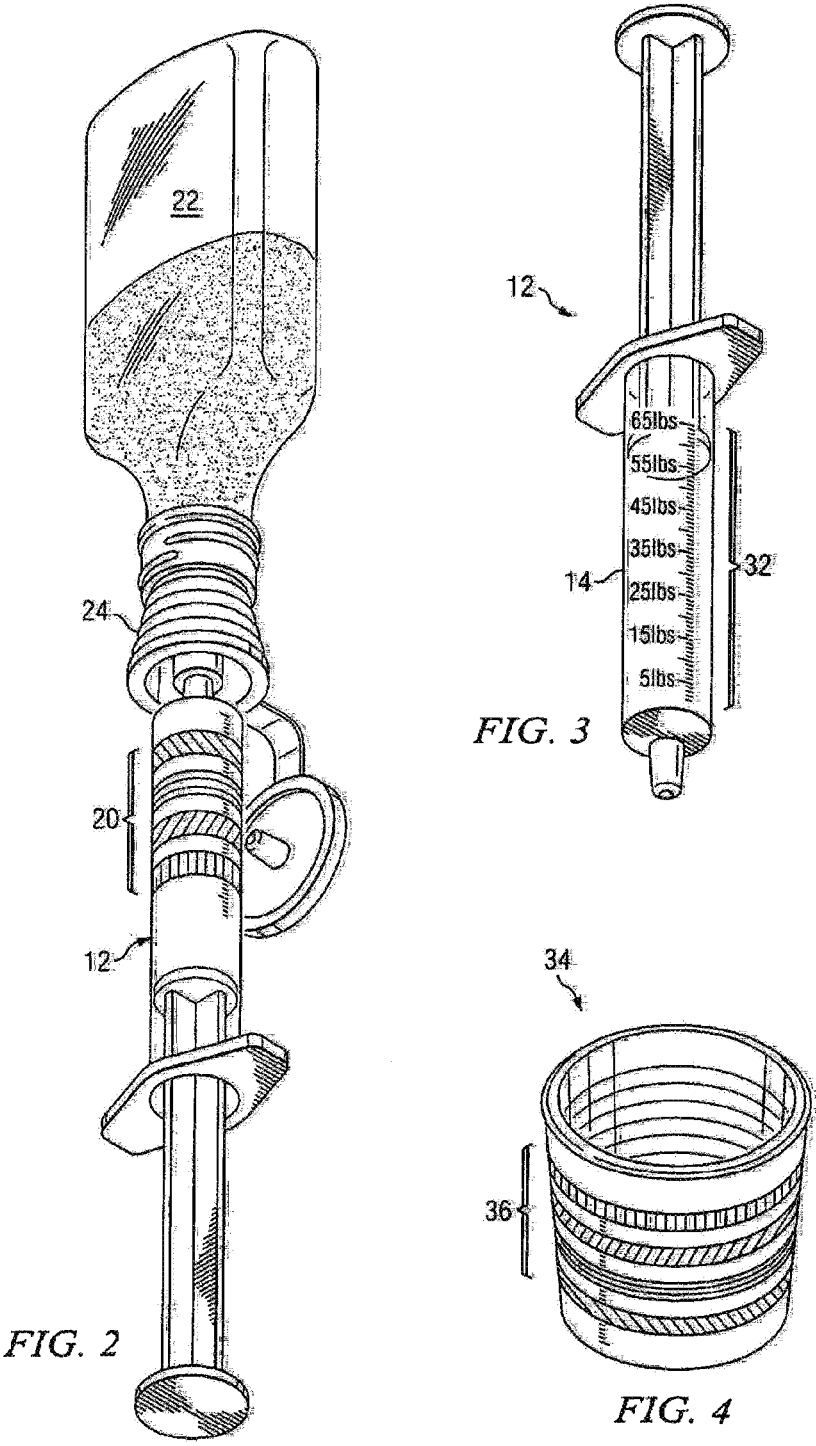

SYSTEM FOR FACILITATING PREPARATION OF MEDICATION DOSES

CROSS-REFERENCE TO RELATED APPLICATIONS

This application is a continuation-in-part of U.S. patent application Ser. No. 14/850,325, filed on Sep. 10, 2015, entitled "System for Facilitating Preparation of Medication Doses," which is a continuation of and claims priority to U.S. patent application Ser. No. 12/196,667 (now U.S. Pat. No. 9,159,249) filed Aug. 22, 2008, which claims priority to U.S. patent application Ser. No. 11/563,901, filed Nov. 28, 2006, now abandoned, which claims the benefit of U.S. Provisional Patent Application No. 60/783,111 filed Mar. 16, 2006, the entire contents of each are incorporated herein by reference.

TECHNICAL FIELD

This present disclosure relates to delivery cups for preparing doses of medication, and more particularly to delivery cups comprising color bands for facilitating the measurement of fluid medications.

BACKGROUND

Many devices and methods for preparing doses of fluid medications are known in the art. For example, it is common when preparing and measuring doses of fluid medications for children to use a syringe to withdraw the fluid from a medicine bottle and then displace the fluid into a child's mouth. Often an adapter is used to firmly and securely engage the syringe with the bottle.

Another device used in the prior art for preparing and measuring doses of medication for children is a tubular container having one closed end for measuring doses and a spoon at the other end for facilitating the displacement of the dose into the child's mouth. Other devices for facilitating the preparation of doses of medication such as measuring cups and medicine droppers are well known in the art.

Common to the prior art discussed above are devices comprised of substantially translucent materials that allow users to see the level of the fluid as it is received in the device. Numeric markings are provided on the translucent material to indicate levels of volume in units of measurement. When preparing doses of medication the user of the device compares the level of fluid in the device to the markings thereon to determine whether the appropriate amount of fluid has been received within the device. Oftentimes the numeric markings are difficult to read or the comparison is difficult to make, especially under low light conditions, or if the medication does not comprise a distinctive color, or if the user of the device has poor eyesight.

SUMMARY

A delivery cup for facilitating preparation of medication doses may provide an opening for receiving a quantity of fluid medication. The delivery cup may provide two opposed ends and at least one sidewall that may extend between the ends, and the two ends and the sidewall may define a maximum volume of the delivery cup. The delivery cup may provide a first color band that may extend about at least a portion of an exterior of the delivery cup, and the first color band may represent the maximum volumetric measurement of the delivery cup. A portion of the delivery cup may be provided to fit inside of an opening of a medicine bottle, and the portion of the delivery cup may be provided to form a tight seal with the opening of the medicine bottle. The color band may correspond to the dose indicator that may be affixed to the medicine bottle. Further, the delivery cup may provide a height that may be proportional to at least one of the maximum volume of the delivery cup and the maximum volumetric measurement. The delivery cup for facilitating preparation of medication doses may include a handle that may be provided on an exterior of the delivery cup. The handle may provide a tab that may form a grip for a thumb and an index finger. The delivery cup for facilitating preparation of medication doses may provide one or more additional color bands that may extend about the exterior of the delivery cup. The one or more additional color bands may represent volumetric measurements that may be less than the maximum volumetric measurement of the delivery cup that may be designated by the first color band.

A system for facilitating preparation of medication doses may include more than one delivery cup to receive a quantity of fluid medication. Each delivery cup may have two opposed ends and at least one sidewall that may extend between the ends. The two ends and the sidewall may define a maximum volume of each of the more than one delivery cup. Further, the system for facilitating preparation of medication doses may provide at least one color band that may extend about at least a portion of an exterior of each of the more than one delivery cup, and each color band may represent the maximum volumetric measurement for a corresponding delivery cup. The system for facilitating preparation of medication doses may provide that each of the more than one delivery cup may have a height that may be proportional to at least one of the maximum volume of each of the more than one delivery cup and the maximum volumetric measurement for the corresponding delivery cup. Additionally, the height of each delivery cup may be different from the height of another delivery cup of the more than one delivery cup. The system for facilitating preparation of medication doses may provide a first delivery cup that may be selected from the more than one delivery cup that may have a first maximum volumetric measurement that may be greater than a second maximum volumetric measurement of a second delivery cup that may be selected from the more than one delivery cup. A first height of the first delivery cup may be greater than a second height of the second delivery cup. The system for facilitating preparation of medication doses may provide the first maximum volumetric measurement that may be approximately twice the second maximum volumetric measurement, and the first height may be approximately twice the second height. Further, the system for facilitating preparation of medication doses may provide a portion of each of the more than one delivery cup that may fit inside of a medicine bottle and may seal the medicine bottle. The system for facilitating preparation of medication doses may include a handle that may be provided on the exterior portion of each of the more than one delivery cup. The handle may provide a tab that may form a grip for a thumb and an index finger. The more than one delivery cup may further include a dose indicator that may be affixed on the medicine bottle. The dose indicator may correspond to each color band that may be provided on each of the more than one delivery cup. A solid color may be provided throughout the delivery cup, wherein the solid color corresponds to each color band provided on each of the more than one delivery cup.

A system for facilitating preparation of medication doses may be provided that may include a delivery cup for receiving a quantity of fluid medication. The delivery cup may include two opposed ends and at least one sidewall extending between the ends, the two opposed ends and the at least one sidewall defining a maximum volume of the delivery cup. A threaded portion may be provided along a first upper portion of the delivery cup configured to threadedly engage a threaded outer portion of a medicine bottle, wherein the threaded outer portion may be provided along a second upper portion of the medicine bottle. A color indicator may be provided on at least a portion of an exterior of the delivery cup, and the color indicator may represent a maximum volumetric measurement. The delivery cup may have a height that may be proportional to at least one of the maximum volume of the delivery cup and the maximum volumetric measurement. A dose indicator may be affixed to the medicine bottle, and the dose indicator may correspond to the color indicator of the delivery cup. The system may further comprise a handle provided on the exterior of the delivery cup. A portion of the delivery cup may be arranged below the threaded inner portion to fit inside of an opening of the medicine bottle, and the portion of the delivery cup may form a tight seal with the opening of the medicine bottle. The color indicator may be selected from at least one of a solid color and a color band.

BRIEF DESCRIPTION OF THE DRAWINGS

A more complete understanding of the present disclosure may be had by reference to the following Detailed Description when taken in connection with the accompanying Drawings, wherein:

FIG. 2 is a perspective view of the embodiment of FIG. 1 illustrating the system in use;

FIG. 3 is a perspective view illustrating a second embodiment of the present disclosure;

FIG. 4 is a perspective view illustrating a third embodiment of the present disclosure;

DETAILED DESCRIPTION

Figure 1:
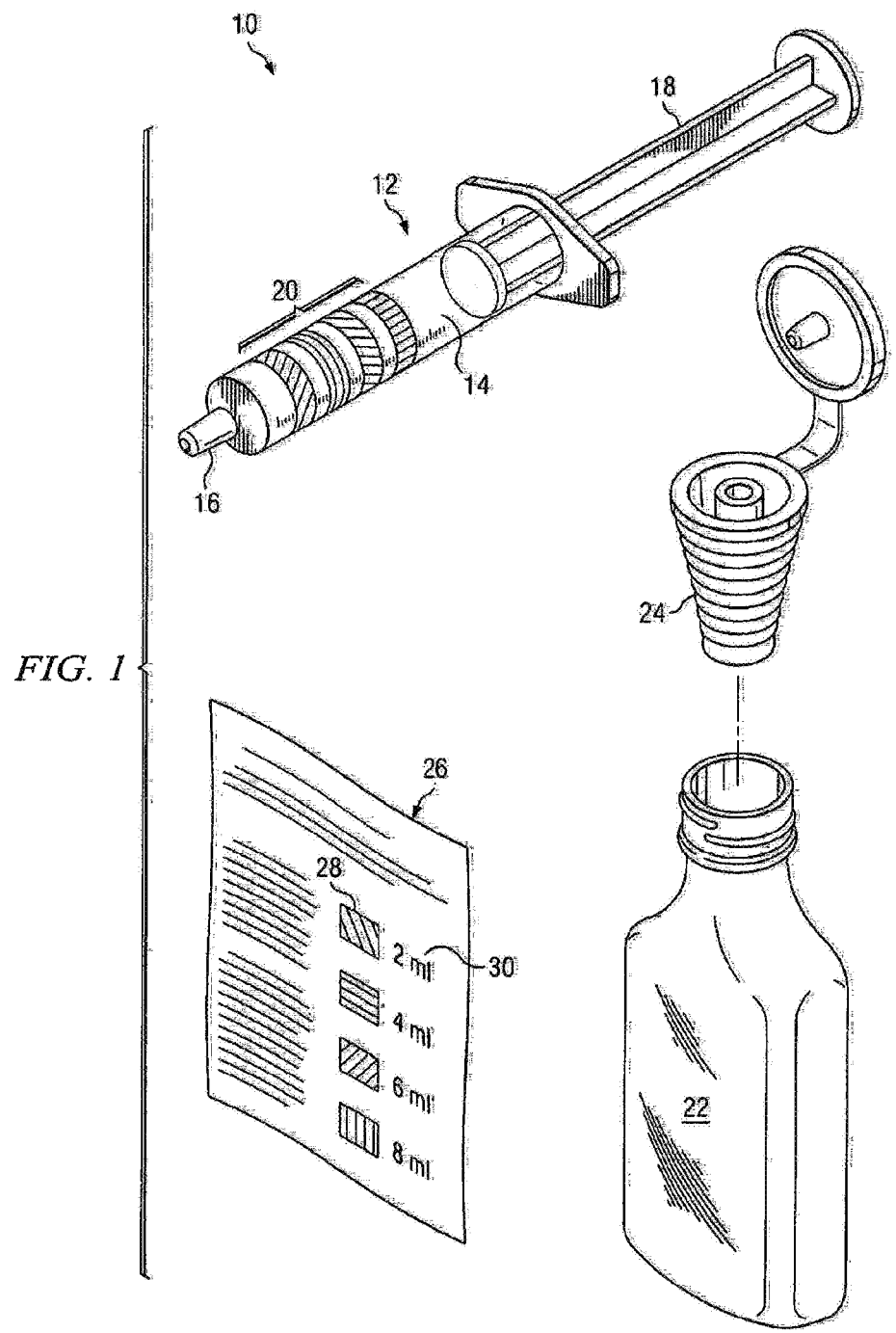
FIG. 1 is a perspective view illustrating a first embodiment of the present disclosure.

Referring to the drawings, and in particular to FIG. 1, there is shown a perspective view of system 10 for facilitating preparation of medication doses comprising a first embodiment of the present disclosure. In particular, there is shown syringe 12 comprising substantially tubular container 14 for receiving a fluid medication through nozzle 16 and plunger 18 for drawing the fluid medication into container 14. A plurality of color bands 20 extend circumferentially around container 14. Color bands 20 enable the user of syringe 12 in determining the amount of fluid that has been drawn into container 14.

Also shown in FIG. 1 is bottle 22 from which the fluid medication is drawn and adapter 24 that is used to securely engage syringe 12 with bottle 22. FIG. 2 illustrates this engagement. Key 26 may be provided for correlating colors 28 comprising color bands 20 with particular volumetric measurements 30.

FIG. 3 illustrates a second embodiment of the present disclosure wherein substantially tubular container 14 comprising syringe 12 is used to receive a fluid medication. In this embodiment, color bands are not used. Instead, marked along substantially tubular container 14 are designations of weight 32 in appropriate units of measurement. The designations of weight 32 correspond to an amount of medication that is appropriate for a human being of a given weight. For example, it may be appropriate for a human being that weighs 35 pounds to have a dose of medication equal to two milliliters.

A third embodiment of the present disclosure is illustrated in FIG. 4. An otherwise conventional fluid medication delivery cup 34 is provided with a plurality of color bands 36. Each of color bands 36 comprises a different color, and each of color bands 36 represents a different unit of volumetric measurement. Cup 34 may be provided with a key which correlates each specific color comprising color bands 36 to a specific unit of volumetric measurement.

Figure 5:
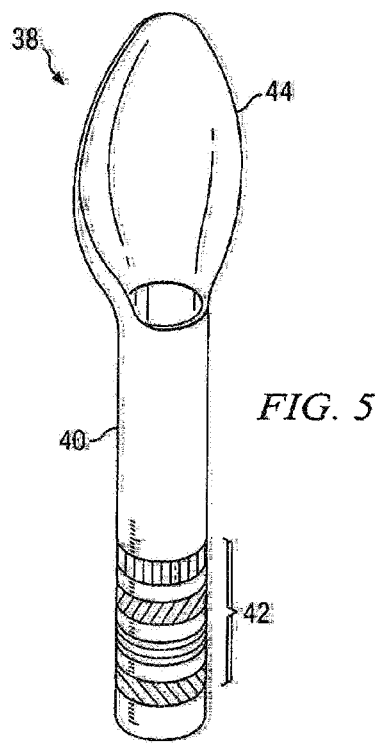
FIG. 5 is a perspective view illustrating a fourth embodiment of the present disclosure.

Medication delivery device 38 comprising a fourth embodiment of the present disclosure is illustrated in FIG. 5. Medication delivery device 38 comprises tubular medication receiving container 40 having a plurality of color bands 42 applied thereto. Each of color bands 42 comprises a different color, and each of color bands 42 correlates to a different unit of volumetric measurement. The end of device 38 remote from color bands 42 comprises spoon 44.

In the use of medication delivery device 38, a fluid medication is introduced into tubular container 40 until the level thereof aligns with a selected color band 42 thereby indicating that the required amount of fluid medication has been received in tubular container 40. Thereafter the medication delivery device is pivoted out of the vertical orientation illustrated in FIG. 5 and into a substantially horizontal orientation whereby the medication from tubular container 40 flows into spoon 44. Spoon 44 is then utilized to deliver the fluid medication into the mouth of a patient.

Figure 6:
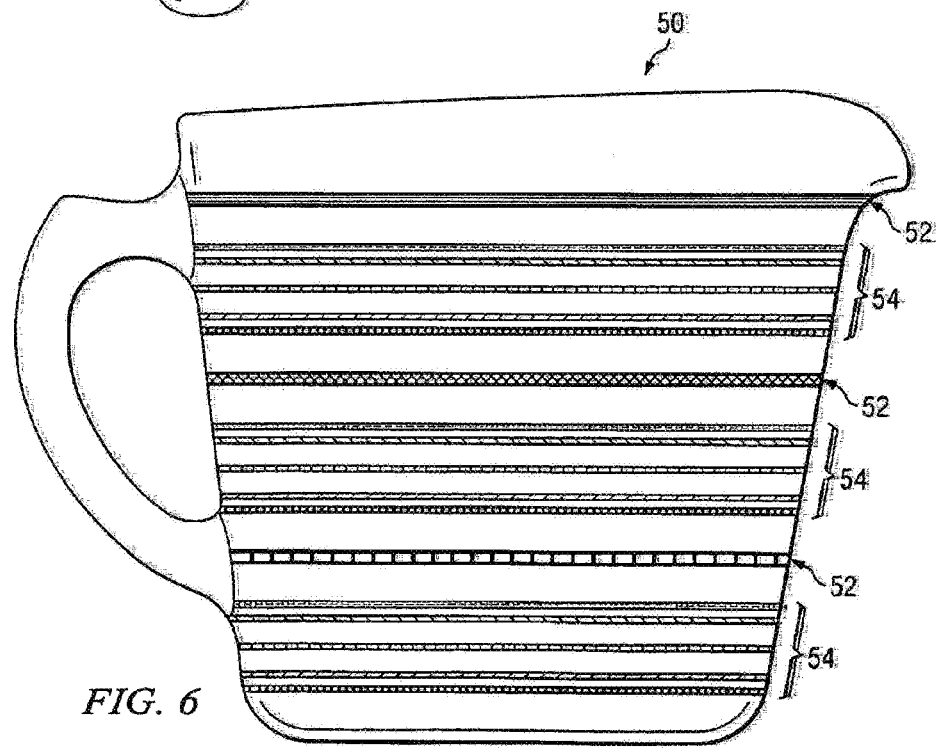
FIG. 6 is a side view illustrating a fifth embodiment of the present disclosure.
Figure 7A:
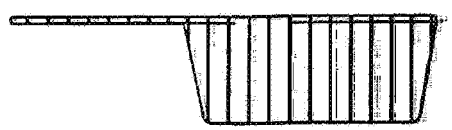
FIGS. 7A through 7F, inclusive, comprise side views illustrating a sixth embodiment of the present disclosure.
Figure 7B:
Figure 7C:
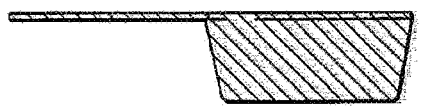
Figure 7D:
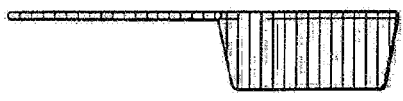
Figure 7E:
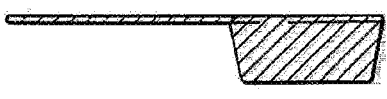
Figure 7F:

Referring to FIG. 6 there is shown measuring cup 50 comprising a fifth embodiment of the present disclosure. Measuring cup 50 is provided with three major color bands 52 each denominating a major unit of volumetric measurement such as 1 cup, 250 milliliters, etc. Measuring cup 50 is further provided with a plurality of minor color bands 54 each denominating a fractional component of the volumetric measurement indicated by major color bands 52. For example, minor color bands 54 may be used to indicate ¼, ⅓, ½, ⅔, and ¾ cup measurements. Minor bands 54 may likewise be used to denominate appropriate subdivisions of major volumetric units expressed in metric terms. The use of measuring cups incorporating the fourth embodiment of the present disclosure greatly simplifies accurate volumetric measurement of fluid medications and other fluids in that it eliminates the need for reading and comprehending numeric symbols.

A set of measuring cups 60 comprising a sixth embodiment of the present disclosure is illustrated in FIGS. 7A-7F, inclusive. In accordance with the present disclosure, each of the measuring cups comprising set 60 thereof is denominated by a different color. For example, the measuring cups comprising set 60 may be manufactured from a selected plastic material having the various colors defining set of measuring cups 60 infused therein such that each measuring cup is comprised entirely of a plastic material characterized by a selected color. Alternatively, the measuring cups comprising set 60 may be differentiated one from another by the colorization of a particular component thereof, for example, the handle. The measuring cups comprising set 60 may also be differentiated one from another by providing a color band similar to the color bands illustrated in FIGS. 1-6 hereof and described hereinabove in conjunction therewith which extends around a predetermined component of the measuring cup.

A feature of the present disclosure comprises the fact that the colors utilized to differentiate the measuring cups comprising set 60 are identical to those utilized to differentiate the various volumetric measurements comprising measuring cup 50 shown in FIG. 6 and described hereinabove in conjunction therewith. Thus, the coloration of the measuring cup shown in FIG. 7A corresponds to the coloring of lowermost major color band 52 of measuring cup 50. The coloration of the measuring cup shown in FIG. 7B corresponds to the coloration of minor color band 54 situated directly beneath lowermost major color band 52 of measuring cup 50, etc. The coordination of the coloring scheme of the measuring cups comprising set 60 with the coloring scheme comprising measuring cup 50 facilitates accurate measurement of fluid materials whether for the dispensing of medications or otherwise. It should be appreciated that according to some embodiments of the present disclosure coordination of the coloring scheme of measuring cups, medication delivery devices, delivery cups, and/or medicine bottles may facilitate accurate measurement of fluid materials, whether for the dispensing of medications or otherwise.

Figure 8:
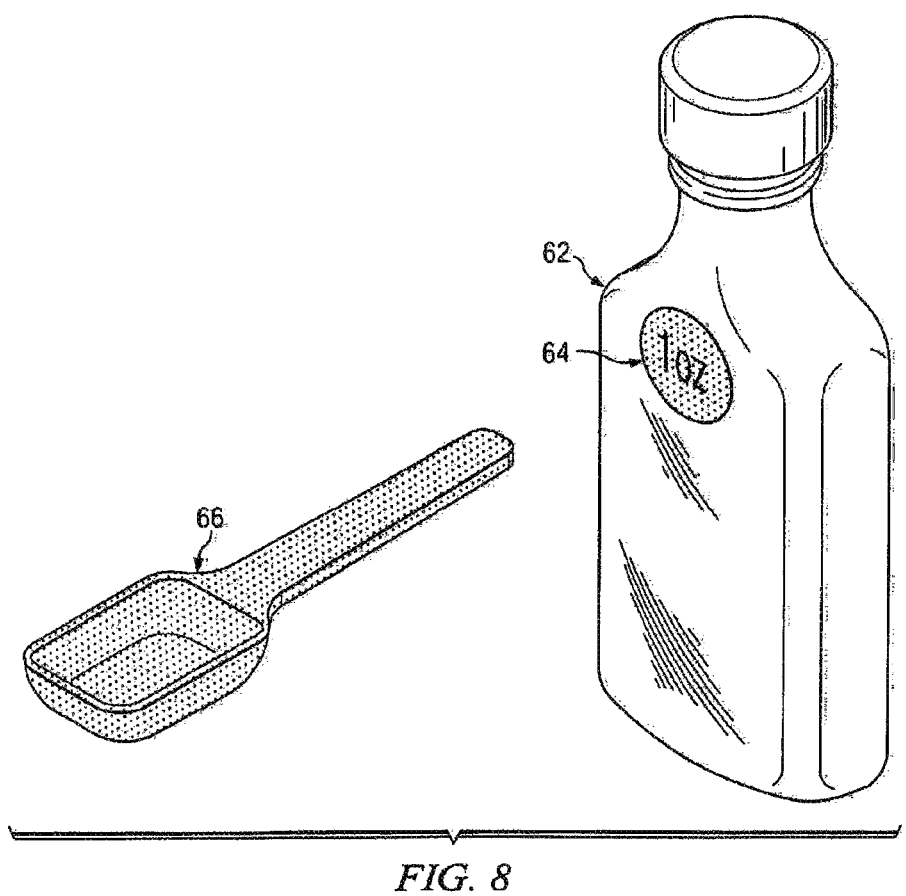
FIG. 8 is a perspective view illustrating a seventh embodiment of the present disclosure.

FIG. 8 depicts a seventh embodiment of the present disclosure. An otherwise conventional medicine bottle 62 is provided with dose indicator 64 comprising a predetermined color. The amount of the prescribed dose corresponding to the predetermined color of dose indicator 64 may be indicated thereon as shown.

The seventh embodiment of the present disclosure further comprises medication dispensing spoon 66. Medication dispensing spoon 66 is characterized by the same predetermined color comprising dosage indicator 64 of medicine bottle 62. Thus, the proper medication dispensing spoon for use in dispensing the medicine contained in medication bottle 62 is easily recognized and selected by simply coordinating the color of dose indicator 64 with the color of medication dispensing spoon 66.

Figure 9:
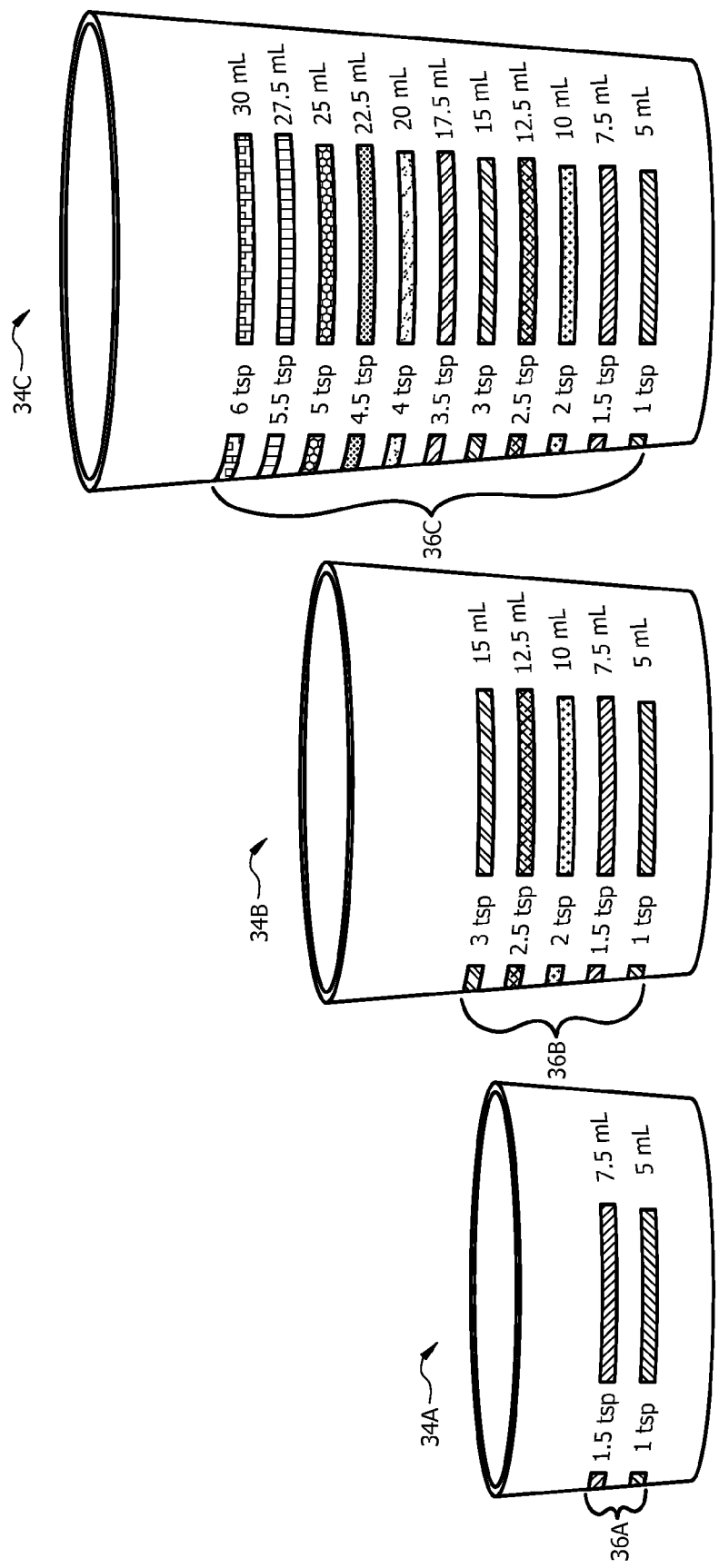
FIGS. 9A through 9C, inclusive, comprise perspective views illustrating an eighth embodiment of the present disclosure.

FIGS. 9A through 9C depict an eighth embodiment of the present disclosure. In accordance with the present disclosure, each of the delivery cups 34A, 34B, and 34C may be provided with a plurality of color bands 36A, 36B, and 36C, respectively. Each color band may comprise a different color and may represent a different unit of volumetric measurement. Delivery cups 34A, 34B, and 34C may each provide two opposed ends and at least one sidewall that may extend between the two opposed ends. The two opposed ends and the sidewall may define a maximum volume of each delivery cup. It should be appreciated that the maximum volume of each delivery cup may correspond to a maximum amount of fluid medication that each delivery cup may hold without overflowing. It should also be appreciated that each delivery cup may hold any fluid. Delivery cups 34A, 34B, and 34C may each have a height that may correspond to a maximum volume and/or a maximum volumetric measurement of each delivery cup. As shown in FIG. 9A according to an embodiment of the present disclosure, delivery cup 34A may have a height that may correspond to a maximum volume and/or a maximum volumetric measurement of delivery cup 34A. The maximum volume and/or the maximum volumetric measurement of delivery cup 34A may be less than a maximum volume and/or a maximum volumetric measurement of another delivery cup that may have a greater height, and each delivery cup may have a height that may be proportional to the maximum volume and/or the maximum volumetric measurement of the delivery cup. For example, delivery cup 34B (FIG. 9B) may provide a maximum volume of 20 mL and a maximum volumetric measurement of 15 mL, and delivery cup 34A (FIG. 9A) may provide a maximum volume of 10 mL and a maximum volumetric measurement of 7.5 mL; as such, delivery cup 34B (FIG. 9B) may provide a height that may be approximately twice the height of delivery cup 34A (FIG. 9A). As shown in FIGS. 9B and 9C according to an embodiment of the present disclosure, delivery cups 34B and 34C, respectively, may provide a height that may be greater than a height of delivery cup 34A (FIG. 9A). As such, delivery cup 34B (FIG. 9B) may have a maximum volume and/or a maximum volumetric measurement that may be greater than a maximum volume and/or a maximum volumetric measurement of delivery cup 34A (FIG. 9A). As shown in FIG. 9C according to an embodiment of the present disclosure, delivery cup 34C may provide a height that may be greater than the height of delivery cups 34A (FIG. 9A) and 34B (FIG. 9B). Further, delivery cup 34C may have a maximum volume and/or a maximum volumetric measurement that may be greater than a maximum volume and/or a maximum volumetric measurement of delivery cups 34A (FIG. 9A) and 34B (FIG. 9B). It should be appreciated that delivery cups 34A, 34B, and 34C may each include color bands 36A, 36B, and 36C that may correspond to any quantity and/or unit of volumetric measurement. It should also be appreciated that delivery cups 34A, 34B, and 34C may not include color bands but may include another form of a color indicator that may be provided on at least a portion of the delivery cup and may correspond to a color indicator provided on at least a portion of a medicine bottle and/or another container in some embodiments of the present disclosure. For example, a first green dot may be provided on an exterior of a delivery cup for dispensing 1 mL of fluid, and an identical second green dot may be provided on an exterior of a medicine bottle that contains the fluid to be dispensed using the delivery cup. Another example may include a green medication dispensing spoon that may be provided to dispense 1 mL of fluid that may correspond to a medicine bottle that may have a green dot provided on the exterior of the medicine bottle that may contain the fluid to be dispensed via the medication dispensing spoon. It should be appreciated that delivery cups 34A, 34B, and 34C may each provide color bands 36A, 36B, and 36C on a first side of delivery cups 34A, 34B, and 34C, respectively, and may provide bands that may not have coloration on a second side of delivery cups 34A, 34B, and 34C opposite of the first side. Bands that may not have coloration may be helpful to individuals who may be colorblind and/or to individuals who may not be able to determine colors. It should be appreciated that delivery cups 34A, 34B, and 34C may include raised patterns and/or raised characters that may indicate a volumetric measurement and/or dosage, particularly for blind individuals, in dark environments, and/or for individuals who may have diminished capacity to see color and/or read numeric symbols. It should be appreciated that delivery cups 34A, 34B, and 36C may/may not include numerals and/or numeric symbols without departing from the present disclosure. It should be appreciated that delivery cups 34A, 34B, and 34C may take any shape. It should also be appreciated that delivery cups 34A, 34B, and 34C may be provided in the form of any type of container. It may be further appreciated that the volume to be dispensed via delivery cups according to embodiments of the present disclosure may be of varying sizes to dispense varying volumes of liquid. In addition, a dispensing cup according to embodiments of the present disclosure may include more or fewer volumetric designations than are depicted in FIGS. 9A, 9B and 9C without departing from the present disclosure.

Figure 10:
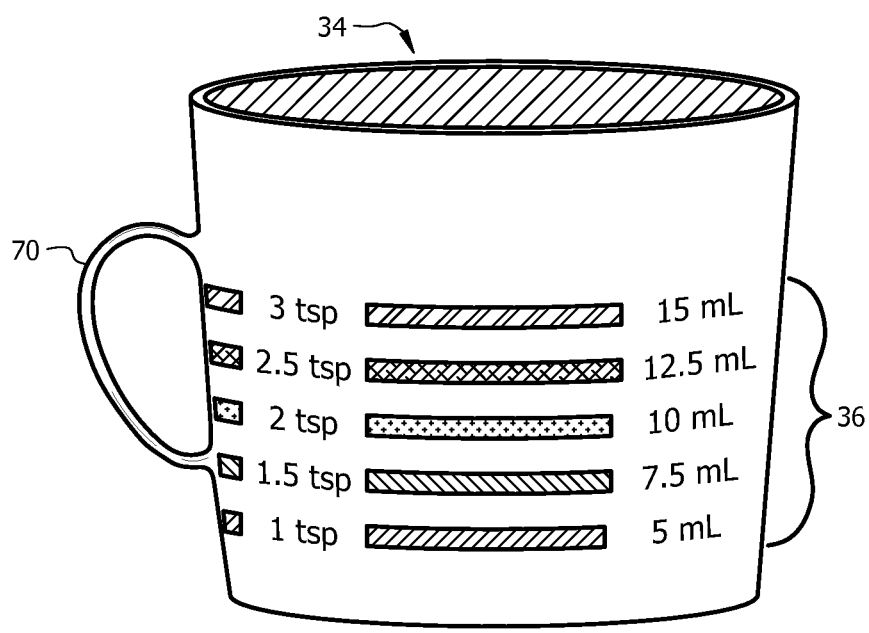
FIG. 10 is a perspective view illustrating a ninth embodiment of the present disclosure.

FIG. 10 depicts a ninth embodiment of the present disclosure. In accordance with the present disclosure, delivery cup 34 may include handle 70 that may provide ease of opening and/or closing a medicine bottle. Further, handle 70 may provide ease of dispensing medicine into and/or from delivery cup 34. Handle 70 may be substantially semi-circular and smooth and may be provided on or attached to an exterior portion of delivery cup 34. Further, handle 70 may provide a tab that may provide a grip for a thumb and an index finger to grasp delivery cup 34. It should be appreciated that handle 70 may be provided in the form of any shape without departing from the present disclosure. It should further be appreciated that handle 70 may be provided at any location along the exterior of delivery cup 34. It should be appreciated that delivery cup 34 may provide a spout or pouring mechanism that may be provided on a side of delivery cup 34 opposite of handle 70 to provide a channel that may dispense fluids from delivery cup 34. Further, delivery cup 34 may include more or fewer color bands than depicted in FIG. 10 without departing from the present disclosure.

Figure 11:
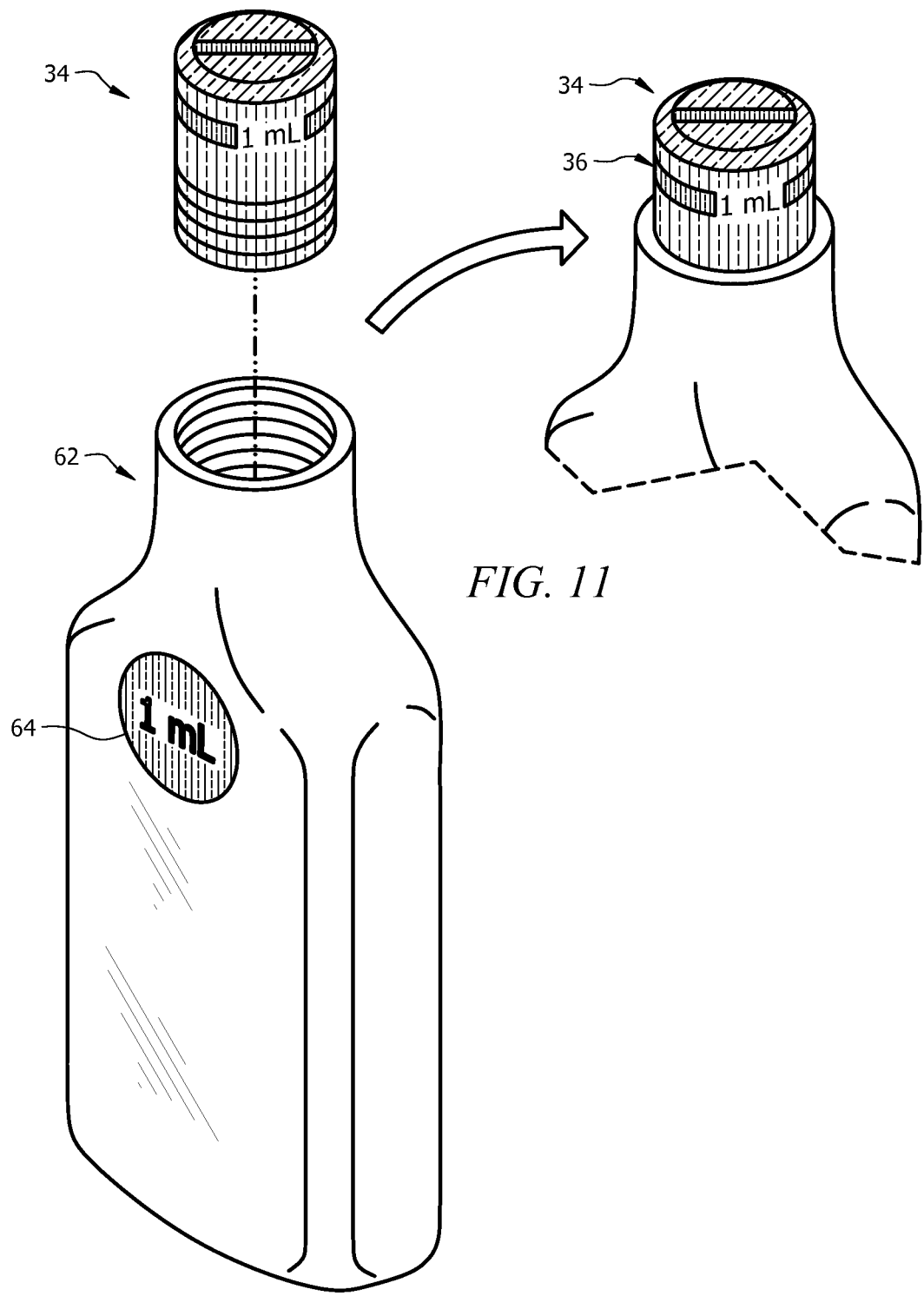
FIG. 11 is a perspective view illustrating a tenth embodiment of the present disclosure.

FIG. 11 depicts a tenth embodiment of the present disclosure. In accordance with the present disclosure, delivery cup 34 may be configured to prevent fluid from dripping down the side of medicine bottle 62. A portion of delivery cup 34 may be provided to fit inside of medicine bottle 62, such that it may form a tight seal and may reduce the likelihood of fluid inadvertently escaping from medicine bottle 62. It should be appreciated that a lower portion of delivery cup 34 may provide a substantially airtight seal. It should further be appreciated that delivery cup 34 may be secured inside of medicine bottle 62 by any attachment means including, but not limited to, a push-fit, a snap-fit, a twisting or screwing motion, and/or via threading that may be provided on delivery cup 34 and/or medicine bottle 62. It should also be appreciated that a top portion of delivery cup 34 may provide a gripping mechanism and/or a larger diameter than a bottom portion of delivery cup 34 that may help to remove delivery cup 34 from medicine bottle 62 and/or to secure delivery cup 34 inside of medicine bottle 62. Delivery cup 34 may include one or more color bands, patterns, and/or symbols that may correspond to any quantity and/or unit of volumetric measurement that may match dose indicator 64 that may be provided on medicine bottle 62. It should be appreciated that color band 36 and dose indicator 64 may include a predetermined color and/or pattern. The amount of a prescribed dose that may correspond to a predetermined color and/or pattern of color band 36 and dose indicator 64 may be indicated thereon as shown in FIG. 11. It should be appreciated that color band 36 may be provided on a top portion and/or a bottom portion of delivery cup 34 without departing from the present disclosure. It should be appreciated that the color indicator may be a solid color that may be provided throughout delivery cup 34 without departing from the present disclosure.

Figure 12:
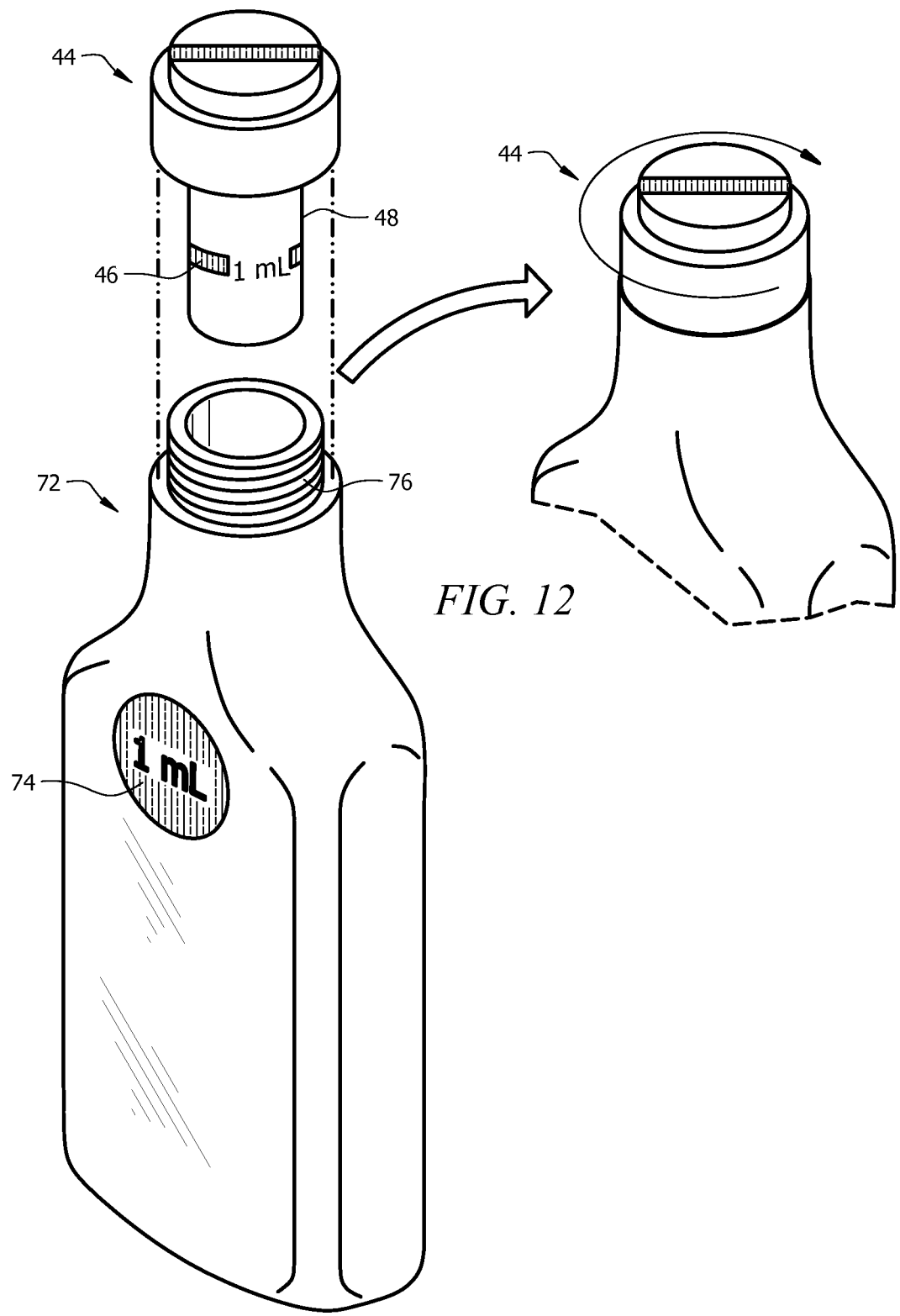
FIG. 12 is a perspective view illustrating an eleventh embodiment of the present disclosure.

FIG. 12 depicts an eleventh embodiment of the present disclosure. In accordance with the present disclosure, delivery cup 44 may be configured to prevent fluid from dripping down the side of medicine bottle 72. Lower portion 48 of delivery cup 44 may be provided to fit inside of medicine bottle 72, such that it may form a tight seal and may reduce the likelihood of fluid inadvertently escaping from medicine bottle 72. Lower portion 48 of delivery cup 44 may include a threaded inner portion (not shown) that may be provided along upper portion of delivery cup 44. Further, the portion of medicine bottle 76 that may be provided to form a tight seal with lower portion 48 of delivery cup 44 may include a threaded outer portion that may be provided along upper portion of medicine bottle 72. As such, a threaded engagement may be formed between an upper portion of delivery cup 44 and medicine bottle 72. It should be appreciated that this threaded engagement may prevent a child from opening the medicine bottle. It should also be appreciated that delivery cup 44 may be provided to seal a standard pharmacy medicine bottle. It should be appreciated that lower portion 48 of delivery cup 44 that may be provided to fit inside of medicine bottle 72 may hold a fluid volume.

It should further be appreciated that delivery cup 44 may be secured inside of medicine bottle 72 by any attachment means including, but not limited to, a push-fit, a snap-fit, a twisting or screwing motion, and/or threading that may be provided on delivery cup 44 and/or medicine bottle 72. It should also be appreciated that the upper portion of delivery cup 44 may provide a gripping mechanism and/or a larger diameter than lower portion 48 of delivery cup 44 that may help to remove delivery cup 44 from medicine bottle 72 and/or to secure delivery cup 44 inside of medicine bottle 72.

Delivery cup 44 may include a color indicator 46 that may provide one or more color bands, patterns, and/or symbols that may correspond to any quantity and/or unit of volumetric measurement that may match dose indicator 74 that may be provided on medicine bottle 72. It should be appreciated that the color indicator may be a solid color that may be provided throughout delivery cup 44 without departing from the present disclosure. It should be appreciated that color band 46 and dose indicator 74 may include a predetermined color and/or pattern. The amount of a prescribed dose that may correspond to a predetermined color and/or pattern of color band 46 and dose indicator 74 may be indicated thereon as shown in FIG. 12. It should be appreciated that color band 46 and/or embossed characters may be provided on a top portion and/or a bottom portion of delivery cup 44 without departing from the present disclosure. It should further be appreciated that delivery cup 44 may be provided in a solid color and may optionally include at least one color band.

Although all of the containers shown in the drawings are depicted as being circular in cross-section, it should be appreciated that the present disclosure is not limited to any particular container shape. Containers utilized according to embodiments of the present disclosure can be oval or elliptical in cross-section. Likewise, containers utilized according to other embodiments of the present disclosure can having cross-sections that are triangular, rectangular, or comprise any number of side walls depending upon the requirements of particular applications of the present disclosure. Containers utilized in further embodiments of the present disclosure may have cross-sectional configurations which are irregular in shape in that they combine one or more linear portions with one or more curvilinear portions.

Although preferred embodiments of the present disclosure have been illustrated in the accompanying Drawings and described in the foregoing Detailed Description, it will be understood that the present disclosure is not limited to the embodiments disclosed, but is capable of numerous rearrangements, modifications, and substitutions of parts and elements without departing from the spirit of the present disclosure.

The invention claimed is:

1. A delivery cup for facilitating preparation of medication doses, comprising:
   an opening for receiving a quantity of fluid medication;
   two opposed ends and at least one sidewall extending between the ends, the two ends and the sidewall defining a maximum volume of the delivery cup;
   a first color band extending about at least a portion of an exterior of the delivery cup, wherein the first color band represents a maximum volumetric measurement of the delivery cup;
   a portion of the delivery cup provided to fit inside of an opening of a medicine bottle, wherein the portion of the delivery cup forms a tight seal with the opening of the medicine bottle, and wherein the color band corresponds to a dose indicator affixed to the medicine bottle; and
   a height that is proportional to at least one of the maximum volume of the delivery cup and the maximum volumetric measurement.

2. The delivery cup for facilitating preparation of medication doses of claim 1, further comprising:
   a handle provided on the exterior of the delivery cup.

3. The delivery cup for facilitating preparation of medication doses of claim 2, wherein the handle provides a tab that forms a grip for a thumb and an index finger.

4. The delivery cup for facilitating preparation of medication doses of claim 1, further comprising:
   one or more additional color bands extending about the exterior of the delivery cup, wherein the one or more additional color bands represent volumetric measurements less than the maximum volumetric measurement of the delivery cup designated by the first color band.

5. A system for facilitating preparation of medication doses, comprising:
   more than one delivery cup for receiving a quantity of fluid medication, each delivery cup having two opposed ends and at least one sidewall extending between the ends, the two ends and the sidewall defining a maximum volume of each of the more than one delivery cup; and
   at least one color band extending about at least a portion of an exterior of each of the more than one delivery cup, wherein each color band represents a maximum volumetric measurement for the corresponding delivery cup, wherein each of the more than one delivery cup has a height proportional to at least one of the maximum volume of each of the more than one delivery cup and the maximum volumetric measurement for the corresponding delivery cup, and wherein the height of each delivery cup is different from the height of another delivery cup of the more than one delivery cup.

6. The system for facilitating preparation of medication doses of claim 5, wherein a first delivery cup selected from the more than one delivery cup has a first maximum volumetric measurement greater than a second maximum volumetric measurement of a second delivery cup selected from the more than one delivery cup, and wherein a first height of the first delivery cup is greater than a second height of the second delivery cup.

7. The system for facilitating preparation of medication doses of claim 6, wherein the first maximum volumetric measurement is approximately twice the second maximum volumetric measurement, and wherein the first height is approximately twice the second height.

8. The system for facilitating preparation of medication doses of claim 5, wherein a portion of each of the more than one delivery cup is provided to fit inside of a medicine bottle and seal the medicine bottle.

9. The system for facilitating preparation of medication doses of claim 8, the more than one delivery cup further comprising:
   a dose indicator affixed on the medicine bottle, wherein the dose indicator corresponds to each color band provided on each of the more than one delivery cup.

10. The system for facilitating preparation of medication doses of claim 5, further comprising:
    a handle provided on the exterior portion of each of the more than one delivery cup.

11. The system for facilitating preparation of medication doses of claim 10, wherein the handle provides a tab that forms a grip for a thumb and an index finger.

12. The system for facilitating preparation of medication doses of claim 5, further comprising:
    a solid color provided throughout the delivery cup, wherein the solid color corresponds to each color band provided on each of the more than one delivery cup.

13. A system for facilitating preparation of medication doses, comprising:
    a delivery cup for receiving a quantity of fluid medication, comprising:
      two opposed ends and at least one sidewall extending between the ends, the two opposed ends and the at least one sidewall defining a maximum volume of the delivery cup;
      a threaded inner portion provided along a first upper portion of the delivery cup configured to threadedly engage a threaded outer portion of a medicine bottle, wherein the threaded outer portion is provided along a second upper portion of the medicine bottle;
      a color indicator provided on at least a portion of an exterior of the delivery cup, wherein the color indicator represents a maximum volumetric measurement;
      a height that is proportional to at least one of the maximum volume of the delivery cup and the maximum volumetric measurement; and
    a dose indicator affixed to the medicine bottle, wherein the dose indicator corresponds to the color indicator of the delivery cup.

14. The system for facilitating preparation of medication doses of claim 13, further comprising:
    a handle provided on the exterior of the delivery cup.

15. The system for facilitating preparation of medication doses of claim 13, further comprising:
    a portion of the delivery cup arranged below the threaded inner portion to fit inside of an opening of the medicine bottle, wherein the portion of the delivery cup forms a tight seal with the opening of the medicine bottle.

16. The system for facilitating preparation of medication doses of claim 13, wherein the color indicator is selected from at least one of a solid color and a color band.

* * * * *